United States Patent [19]

Yamamoto et al.

[11] Patent Number: 5,354,644
[45] Date of Patent: Oct. 11, 1994

[54] PHOTORESIST COMPOSITIONS COMPRISING STYRYL COMPOUND

[75] Inventors: Takanori Yamamoto, Minoo; Shinji Konishi, Takatsuki; Ryotaro Hanawa, Ibaraki; Akihiro Furuta, Takatsuki; Takeshi Hioki, Osaka; Jun Tomioka, Takarazuka, all of Japan

[73] Assignee: Sumitomo Chemical Company, Limited, Osaka, Japan

[21] Appl. No.: 937,684

[22] Filed: Sep. 1, 1992

Related U.S. Application Data

[62] Division of Ser. No. 290,264, Dec. 27, 1988, Pat. No. 5,218,136.

[30] Foreign Application Priority Data

Dec. 28, 1987 [JP] Japan .................. 62-332110
Jul. 15, 1988 [JP] Japan .................. 63-177752

[51] Int. Cl.⁵ .................. G03C 1/72; G03C 1/52
[52] U.S. Cl. .................. 430/270; 430/926; 430/191
[58] Field of Search .......... 430/325, 326, 926, 191, 430/177, 196, 270

[56] References Cited

U.S. PATENT DOCUMENTS

| | | | |
|---|---|---|---|
| 3,331,687 | 7/1967 | Kosche et al. | 96/1.5 |
| 4,420,555 | 12/1983 | Kruegger et al. | 430/507 |
| 4,439,372 | 3/1984 | Hugl et al. | 558/374 |
| 4,927,732 | 5/1990 | Merrem et al. | 430/191 |
| 5,043,243 | 8/1991 | Yajima et al. | 430/191 |
| 5,066,567 | 11/1991 | Merrem et al. | 430/325 |

FOREIGN PATENT DOCUMENTS

| | | |
|---|---|---|
| 0029412 | 11/1980 | European Pat. Off. |
| 0231522 | 12/1986 | European Pat. Off. |
| 0312950 | 4/1989 | European Pat. Off. |
| 61-93445 | 5/1985 | Japan |

OTHER PUBLICATIONS

Chem. Abs. 105:216698t (1986) *Novel photoresist compositions*.

*Primary Examiner*—Marion E. McCamish
*Assistant Examiner*—Rosemary Ashton
*Attorney, Agent, or Firm*—Birch, Stewart, Kolasch & Birch

[57] ABSTRACT

A photoresist composition which includes a sensitizing compound, a resin and, as a light absorber, a styryl compound of the formula:

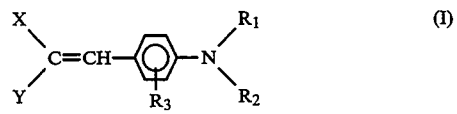

or

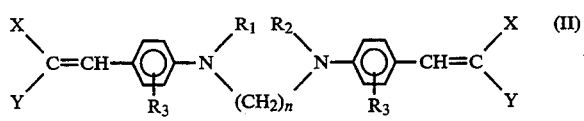

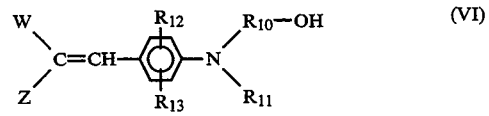

wherein $R_1$, $R_2$ and $R_{11}$ are the same or different and a hydrogen atom, an optionally substituted alkyl, alkenyl or aralkyl group or $R_1$ and $R_2$ may form a ring together with the nitrogen atom to which they are bonded, which ring may include at least one hetero atom in addition to said nitrogen atom; $R_{10}$ is an optionally substituted alkylene group; $R_3$ is —OH, —OCOR$_5$ or —OSi(R$_5$)$_3$ in which $R^5$ is an alkyl group; $R_{12}$ and $R_{13}$ are independently a hydrogen atom, an optionally substituted lower alkyl or alkoxy group, an amide group or a halogen atom; X, Y, W and Z are the same or different and an electron attracting group, and n is a number of 2–15.

5 Claims, No Drawings

PHOTORESIST COMPOSITIONS COMPRISING STYRYL COMPOUND

This application is a divisional of copending application Ser. No. 07/290,264, filed on Dec. 27, 1988 not U.S. Pat. No. 5,218,136 issued Jun. 8, 1993, the entire contents of which are hereby incorporated by reference.

BACKGROUND OF THE INVENTION

1. Field of the Invention

The present invention relates to styryl compounds, a process for preparing said styryl compounds and photoresist compositions comprising said styryl compounds, which photoresist compositions can be preferably used to form fine patterns on a substrate having high reflectance in the production of semiconductors.

2. Description of the Related Art

A photoresist which comprises a sensitizing compound having a quinone diazide group and a novolak resin, or which comprises a bisazide sensitizer and a cyclized rubber is used in the production of integrated circuits such as LSI.

In a process for producing the integrated circuits, fine patterns are formed on various substrates through photoresists. However, when the conventional photoresists are used on the substrates having high reflectance such as those made of aluminum, aluminum-silicon, polysilicon and the like, various problems arise. For example, a region which should not be exposed may be exposed because of reflection on a surface of the substrate and/or side walls of steps. This phenomenon is generally called as notching or halation.

To solve these problems and prevent deterioration of resolution, Japanese Patent Publication No. 37562/1976 proposes a photoresist composition which comprises, as a light absorber, a dye represented by the formula:

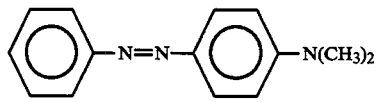

having characteristic, absorptions in the ultraviolet range(Oil Yellow [C.I. 11020]). This photoresist composition can decrease light transmission through the photoresist layer and reduce the undesirable exposure of the substrate.

In the context of the specification, a "photoresist" is intended to mean a composition which comprises a sensitizer and a resin such as novolak, and a "photoresist composition" is intended to mean a composition which comprises a "photoresist" and a light absorber.

In general, if the light absorber is added to the photoresist, undesirable problems may arise. For example, photoresist drastically loses its sensitivity and productivity of the semiconductors is decreased.

The photoresist layer is usually formed by applying the photoresist composition containing a solvent on a wafer and prebaking the wafer with the applied photoresist composition to evaporate off the solvent. However, some light absorbers may precipitate during storage of the photoresist composition, or sublimate during prebaking so that a concentration of the light absorber in the photoresist layer formed on the wafer may be lowered, which lead to unsatisfactory results or variation of quality of the produced semiconductors.

To solve these problems, phenylazobenzene derivatives are proposed in Japanese Patent Kokai (Laid-open) Publication Nos. 368358/1980 and 174941/1983. But, the use of such derivatives creates some problems. For example, the phenylazobenzene derivatives should be used in a large amount in order to obtain sufficient absorption at desired wavelength, especially when the prebaking temperature is raised, or such derivatives have inferior anti-sublimation, a broad absorption range, low absorbing performance and undesirable absorption at certain wavelength. Japanese Patent Kokai Publication No. 93445/1986 discloses a photoresist composition comprising, as a light absorber, a certain styryl compound. Although the disclosed styryl compound can solve the problems associated with the prebaking, it greatly decreases the sensitivity of the photoresist.

SUMMARY OF THE INVENTION

An object of the present invention is to provide a novel styryl compound which is useful as a light absorber in the photoresist composition suitable for microlithography.

Another object of the present invention is to provide a process for preparing the novel styryl compound.

A further object of the present invention is to provide a light absorber which does not sublimate during prebaking of a photoresist composition applied on a substrate or does not precipitate during storage of the composition and has good compatibility with a photoresist.

A yet another object of the present invention is to provide a photoresist composition suitable for forming fine patterns having high resolution on a substrate having high reflectance without causing any halation or notching.

A yet further object of the present invention is to provide a photoresist composition which is stable against the prebaking of the substrate and suffers from less deterioration of sensitivity caused by the addition of the light absorber.

As the result of the extensive study, it has been found that the styryl compound of the following formula (I), (II) or (VI) accomplishes the above objects and solves the problems associated with the prior arts. The present invention has been completed based on this finding.

According to the first aspect of the present invention, there is provided a compound of the general formula:

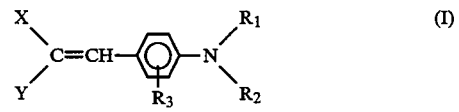

or

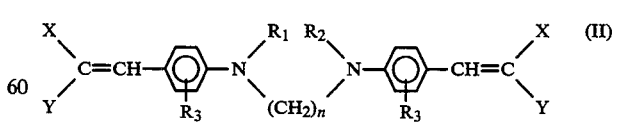

wherein $R_1$ and $R_2$ are the same or different and a hydrogen atom, an optionally substituted alkyl group, an optionally substituted alkenyl group or an optionally substituted aralkyl group or $R_1$ and $R_2$ may form a ring together with the nitrogen atom to which they are bonded, which ring may include at least one hetero atom in addition to said nitrogen atom; $R_3$ is —OH, —OCOR$_5$ or —OSi(R$_5$)$_3$; X and Y are the same or different and are

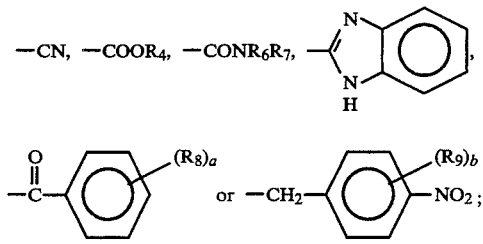

$R_4$ and $R_5$ are each an alkyl group; $R_6$, $R_7$, $R_8$ and $R_9$ are the same or different and a hydrogen atom, an optionally substituted lower alkyl or phenyl group; n is a number of 2 to 15; and a and b are the same or different and a number of 1 to 2.

According to the second aspect of the present invention there is provided a process for preparing the compound of the general formula (I) or (II), which comprises reacting a compound of the general formula:

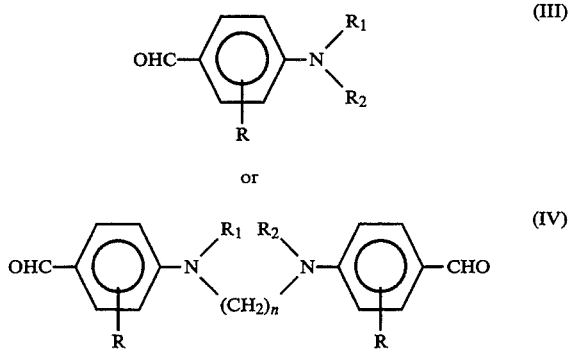

wherein $R_1$, $R_2$ and n are same as defined above; and R is —OCOR$_5$ or —OSi(R$_5$)$_3$ with a compound of the general formula:

wherein X and Y are same as defined above.

According to the third aspect of the present invention, there is provides a photoresist composition which comprises the compound of the general formula (I) or (II).

According to the fourth aspect of the present invention, there is provided a photoresist composition which comprises a compound of the general formula:

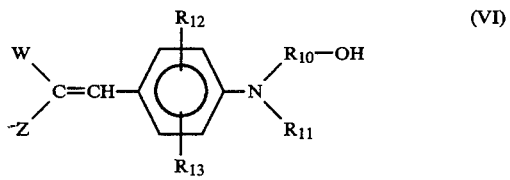

wherein W and Z are the same or different and an electron attractive group; $R_{10}$ is an optionally substituted $C_1$-$C_{10}$ alkylene group, $R_{11}$ is a hydrogen atom, an optionally substituted $C_1$-$C_{10}$ alkyl, alkenyl or aralkyl group; and each of $R_{12}$ and $R_{13}$ is a hydrogen atom, an optionally substituted lower alkyl group, an optionally substituted lower alkoxy group, an amide group or a halogen atom.

DETAILED DESCRIPTION OF THE INVENTION

In the general formulae (I) and (II), preferably, each of $R_1$ and $R_2$ is a hydrogen atom or an alkyl, alkenyl or aralkyl group which has up to 10 carbon atoms, particularly up to 8 carbon atoms and may optionally has at least one substituent. Examples of the substituent are

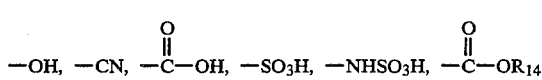

(in which $R_{14}$ is a lower alkyl group) or a halogen atom such as fluorine, chlorine, bromine or iodine. Among the substituents, —OH and —CN are preferable.

Each of $R_4$ and $R_5$ is preferably a $C_1$-$C_4$ alkyl group.

n is preferably a number of 3 to 9.

Each of X and Y is preferably

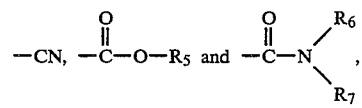

particularly —CN and —C(=O)—O—R$_5$.

The compound (I) may be prepared by a condensation reaction of the compound (III) with the compound (V) and the compound (II) may be prepared by a condensation reaction of the compound (IV) with the compound (V).

The condensation reaction may be carried out in an inert organic solvent. Examples of the inert organic solvents are ethanol, n-propanol, toluene, chlorobenzene, chloroform, dimethylformamide, N-methylpyrolidone, dimethylsulfoxide, sulfolane, acetonitrile, acetic anhydride and mixtures thereof.

The compound (III) is mixed with the compound (IV) in the inert organic solvent. Then, a catalyst is added to the mixture. The catalyst is preferably an organic base such as, piperidine, pyridine, triethylamine and a mixture of piperidine and glacial acetic acid. The reaction mixture is kept at a temperature of from 0° to 100° C., preferably from 20° to 80° C., for 0.5 to 20 hours, preferably for 1 to 10 hours to proceed the condensation reaction. Then, the solvent is removed from the reaction mixture to leave a crude cake of the compound of the formula (I) or (II). The crude cake can be purified by a conventional method, for example, recrystallization from an adequate solvent such as those used in the condensation reaction. When the compound (I) or (II) contains the hydroxyl group as the substituent in $R^1$ or $R^2$ or when $R^3$ is the hydroxyl group, the hydroxyl group can be derived through hydrolysis of a corresponding hydrolyzable group.

The compound of the formula (I) or (II) is added to a photoresist to prepare the photoresist composition of the present invention. Any conventional positive or negative photoresist can be used according to the present invention. A photoresist which comprises a novolak resin and a naphthoquinone diazide compound is preferably used. The novolak resin is obtained through the addition condensation reaction of a phenol compound with formaldehyde.

Also, a photoresist which comprises a cresol novolak resin and an ester of polyhydroxybenzophenone with naphthoquinone-1,2-diazide sulfonic acid is preferably used. The cresol novolak resin can be prepared by a reaction of meta-cresol and/or para-cresol with formalin, or a reaction of meta-cresol, para-cresol and 3,5-xylenol with formalin. Examples of the polyhydroxybenzophenone are 2,3,4-trihydroxybenzophenone 2,3,4,4'-tetrahydroxybenzophenone, 2,2',4,4'-tetrahydroxybenzophenone, 2,3,3',4-tetrahydroxybenzophenone, 2,2',3,4,5-pentahydroxybenzophenone, 2,3,3',4,5-pentahydroxybenzophenone, 2,3,3',4,4'-pentahydroxybenzophenone, 2,2',3,4,4'-pentahydroxybenzophenone, 2,2',3,3',4-pentahydroxybenzophenone, and the like.

Among the compounds of the formula (I) or (II), those having absorption in a wavelength range not longer than 550 nm, particularly between 350 to 400 nm are preferably used in the photoresist composition.

Preferred examples of the compounds (I) which are suitable as the light absorber in the photoresist composition according to the present invention are as follows. These examples will not limit the scope of the present invention.

-continued
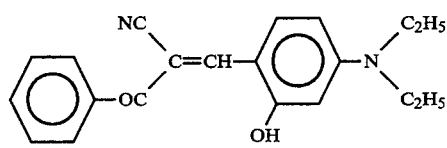 (17)
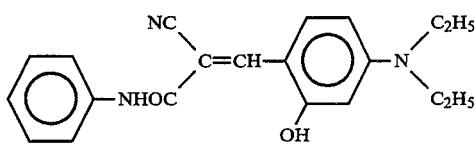 (18)
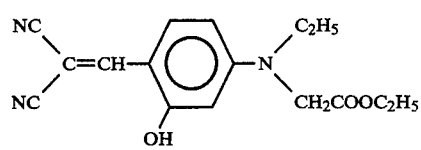 (19)
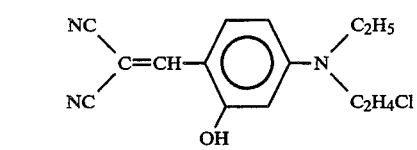 (20)
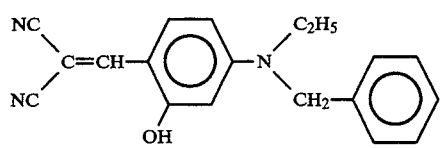 (21)
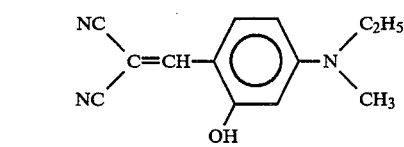 (22)
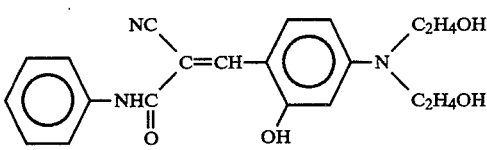 (23)
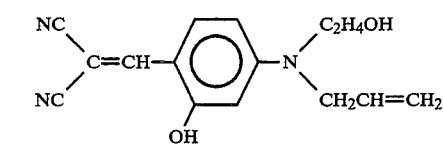 (24)
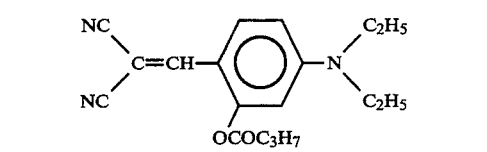 (25)
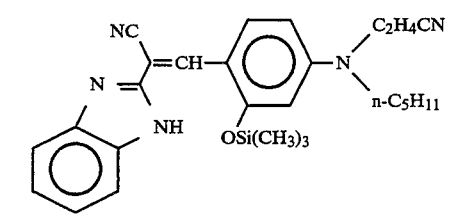 (26)
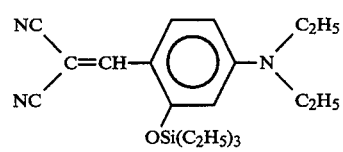 (27)
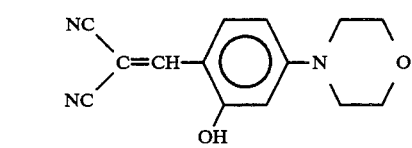 (28)
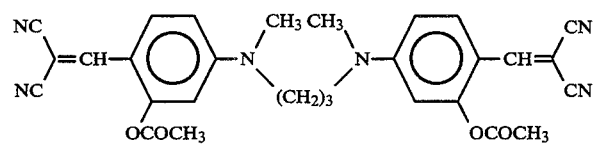 (29)
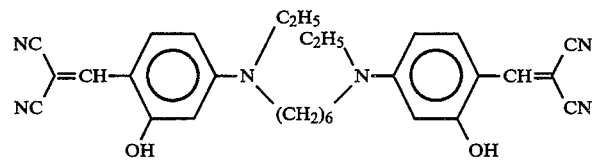 (30)
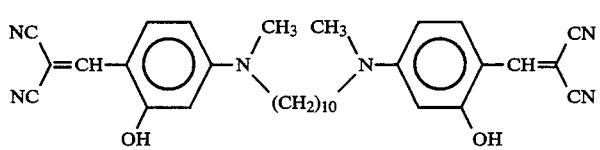 (31)
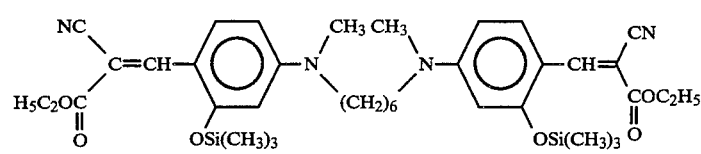 (32)

-continued

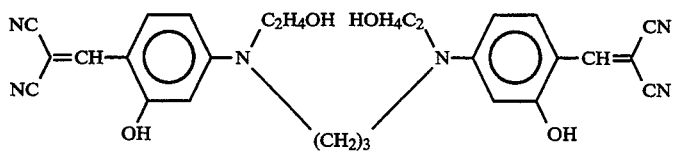   (33)

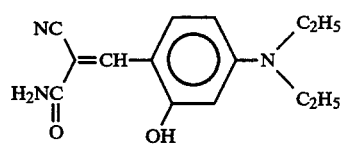   (34)

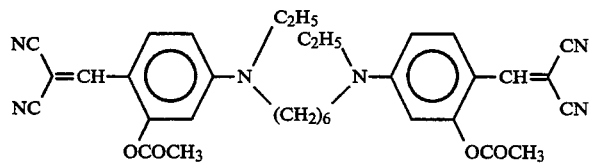   (35)

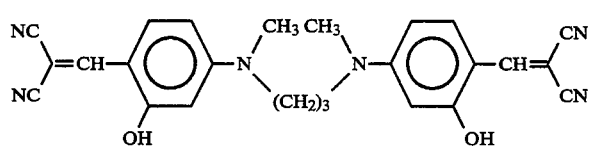   (36)

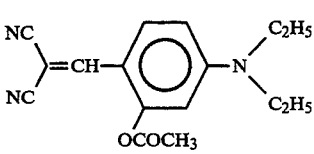   (37)

The amount of the compound (I) to be added to the photoresist composition is from 0.1 to 20% by weight, preferably from 0.2 to 10% by weight based on the weight of the solid component in the photoresist.

The amount of the compound (II) to be added to the photoresist composition is from 0.1 to 15% by weight, preferably from 0.1 to 8% based on the weight of the solid component in the photoresist.

If the amount of the compound (I) or (II) is smaller than the above lower limit, the photoresist composition cannot prevent the halation sufficiently. If the amount of the compound (I) or (II) exceeds the above upper limit, the photoresist composition tends to have inferior profile or sensitivity.

The photoresist composition may optionally contain at least one other light absorber.

The photoresist composition of the present invention can be prepared also by adding the compound (VI) to the photoresist.

The photoresist used in this case is the same as the above one. In the general formula (VI), W, Z, $R_{10}$, $R_{11}$, $R_{12}$ and $R_{13}$ are as defined above. Each of W and Z is preferably

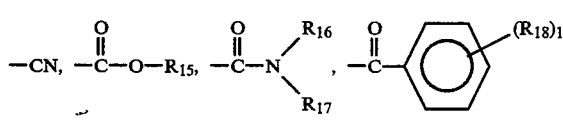

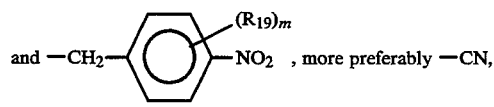, more preferably —CN,

-continued

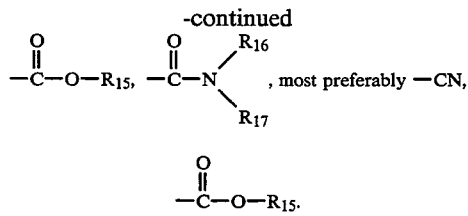, most preferably —CN,

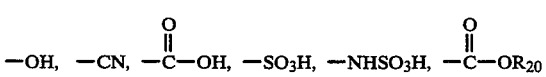

$R_{10}$ is preferably an optionally substituted $C_1$–$C_8$ alkylene group, $R_{11}$ is preferably an optionally substituted lower alkyl, alkenyl or aralkyl group, and each of $R_{16}$ to $R_{19}$ is a hydrogen atom, an optionally substituted lower alkyl group or a phenyl group.

Each of l and m represents a number of 1 to 2.

Examples of the substitutes which is optionally bonded to the above groups are

—OH, —CN, $-\overset{O}{\underset{\|}{C}}-OH$, —$SO_3H$, —$NHSO_3H$, $-\overset{O}{\underset{\|}{C}}-OR_{20}$ (wherein $R_{20}$ is a lower alkyl group), and a halogen atom. Particularly, —OH and —CN are preferable.

In this specification, the "lower" used in connection with the alkyl or alkoxy group or other groups is intended to mean that the group contains 1 to 10 carbon atoms, preferably 1 to 8 carbon atoms.

Most of the compounds of the formula (VI) are known from U.S. Pat. No. 4,439,372 or J. of the Society of Dyers and Colourists, April (1977) 126–133. Then, the compounds (VI) can be easily prepared by the method described in the above literatures or analogous methods thereto. Among the compounds (VI), those having the maximum absorption in a wavelength range not longer than 550 nm, particularly between 350 nm and 400 nm are preferably used in the photoresist composition.
Examples of the compounds (VI) which are suitable as the light absorber in the photoresist composition are as follows. These examples will not limit the scope of the present invention.
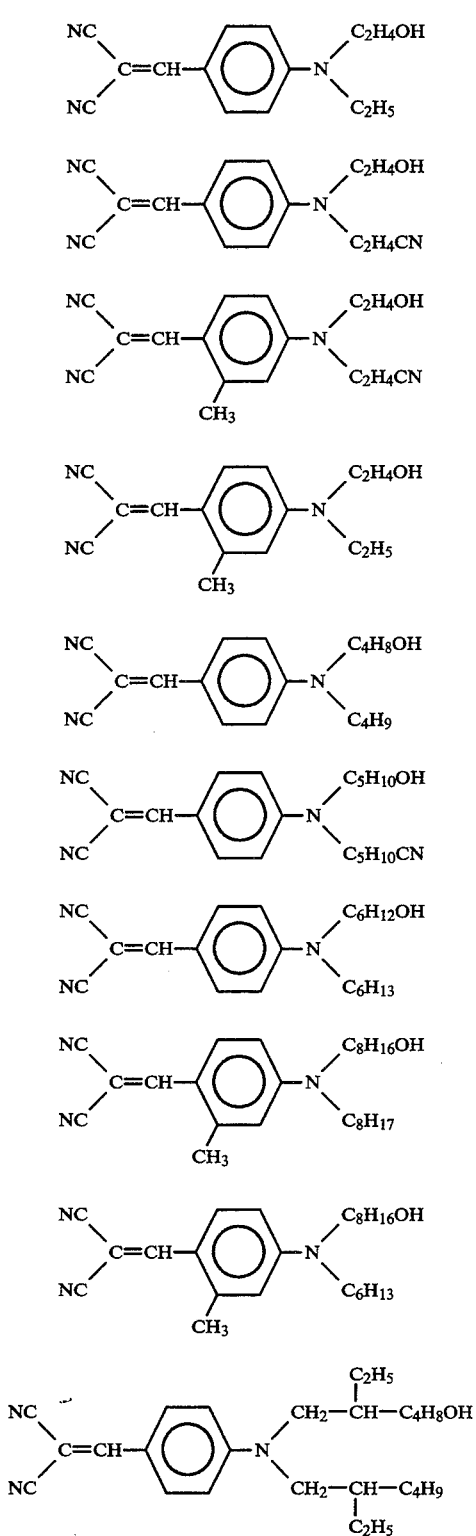
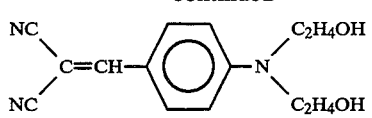
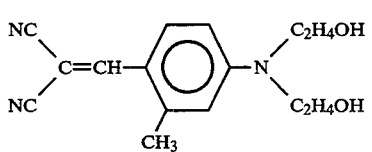
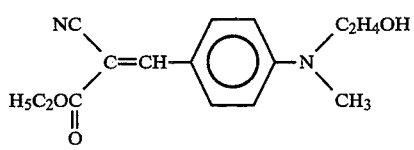
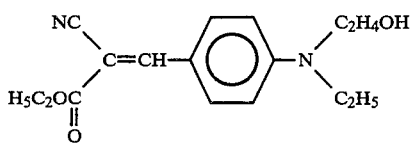
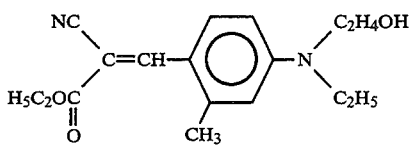
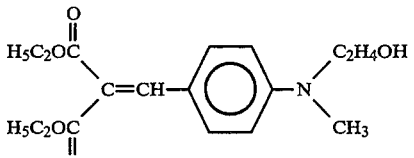
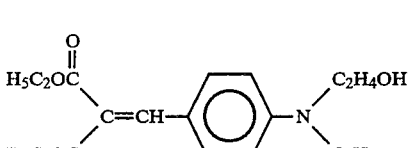
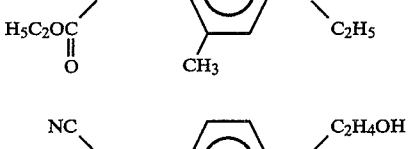
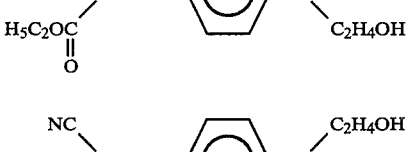
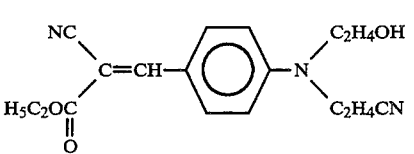

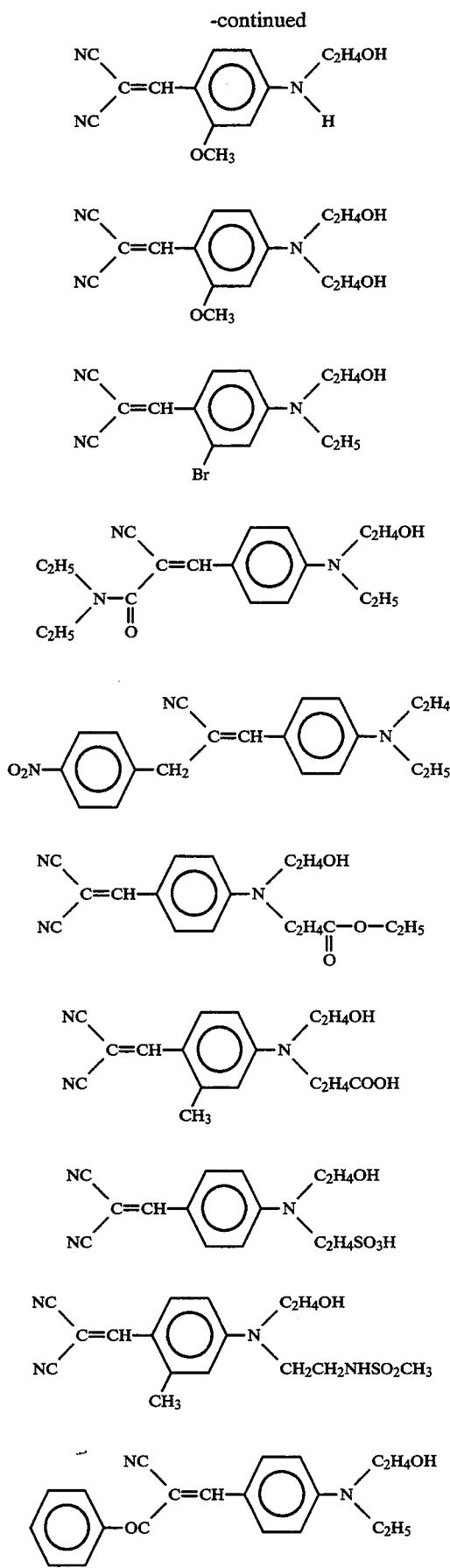
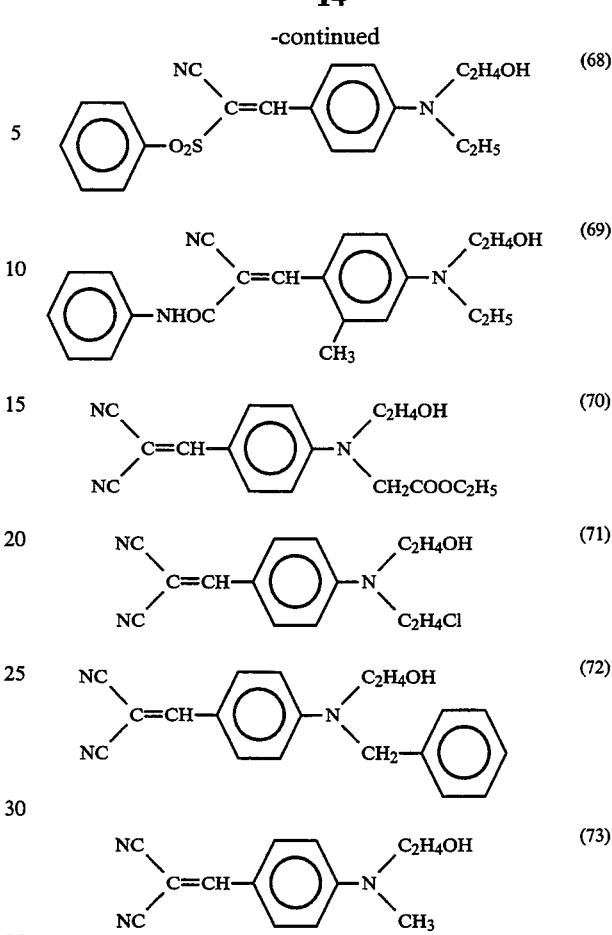

The amount of the compound (VI) to be added to the photoresist composition is from 0.1 to 20%, preferably from 0.2 to 10% based on the weight of the solid component in the photoresist. If the amount of the compound (VI) is smaller than the above lower limit, the photoresist composition cannot prevent the halation sufficiently. If the amount of the compound (VI) exceeds the above upper limit, the photoresist composition tends to have inferior profile or sensitivity. The photoresist composition may optionally contain at least one other dye compound.

As described above, the compound (VI) is prepared by the known processes. The typical processes are as follows:

(1) An amine is subjected to formylation according to the Vilsmeyer reaction and then reacted with an active methylene component to obtain the compound (VI).

(2) An amine is converted to a Schiff base and then reacted with an active methylene component to obtain the compound (VI).

In the process (1) or (2), to suppress side reactions and improve a yield of the desired product, prior to the formylation in the process (1) or the conversion to the Schiff base, an active group in the amine is protected through esterification, and the esterified active group is hydrolyzed before or after the reaction with the active methylene component.

In addition to the light absorber in the photoresist composition, the compounds (I) and (II) can be used as coloring materials in dying, sublimation thermal transfer printing, color filters, etc.

The styryl compounds of the formulae (I), (II) and (VI) are easily dissolved in organic solvents such as xylene, ethyl cellosolve, cyclohexanone, cellosolve acetate, butyl acetate, etc. These styryl compounds has good compatibility with the rubber base photoresists and also deep U.V. resists. Because the styryl compounds do not sublimate even at high temperatures, a photoresist composition which comprises the compound (I), (II) or (VI) can be pre-baked at high temperatures to remove the solvent completely so that the uniform photoresist layer can be formed on the substrate. In addition, since the photoresist composition according to the present invention has good antihalation effect, fine patterns can be formed on the substrate with good reproducibility.

Since styryl compounds of the present invention do not precipitate even after long storage, an uneven coating due to the precipitation can be prevented.

With the photoresist compositions according to the present invention, the problems associated with the prior arts can be solved, and patterns with high resolution can be formed on the substrate having high reflectance.

PREFERRED EMBODIMENTS OF THE INVENTION

The present invention will be illustrated more in detail with the following examples, but it is not limited to these examples.

EXAMPLE 1

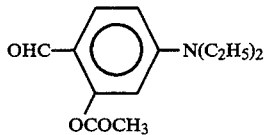

was mixed with 0.79 g of a compound of the formula:

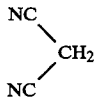

in 20 ml of ethanol followed by stirring for 6 hours at 22°–25° C.

Then ethanol was distilled off from the mixture to obtain a crude cake, which was recrystallized from ethanol to obtain a purified cake (2.12 g) of the compound of the formula:

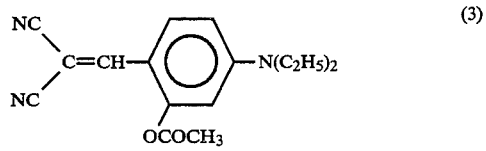

Melting point: 106°–107° C.

Absorbance of the compound (3) in ethyl cellosolve acetate:

$\lambda_{max}$: 436 nm $\epsilon : 6.53 \times 10^4$

EXAMPLE 2

To a mixture of 2.00 g of the compound (3) obtained in Example 1 and 70 ml of ethanol, 6 ml of conc. HCl aq was added and stirred for 2 hours at 55°–60° C. After cooling down to 20°–22° C., the resulting precipitate was filtered off to obtain 1.35 g of a crude cake. The crude cake was recrystallized from ethanol to obtain a purified cake (1.35 g) of the compound of the formula (4):

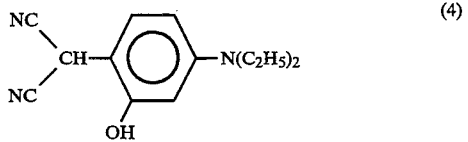

Melting point: 235°–236° C.

Absorbance of the compound (4) in ethyl cellosolve acetate:

$\lambda_{max}$: 421 nm $\epsilon: 5.01 \times 10^4$

EXAMPLES 3–12

In a similar manner to that described in Examples 1 and 2, compounds shown in Table 1 were prepared.

TABLE 1

| Ex. No. | Chemical structure | Maximum absorbing wavelength (nm) in ethyl cellosolve acetate |
| --- | --- | --- |
| 3 | NC\\>=CH—⟨○⟩—N(n-C4H9)2, NC/, OH | 439 |
| 4 | NC\\>=CH—⟨○⟩—N(C2H5)2, H2NOC/, OH | 398 |

TABLE 1-continued

| Ex. No. | Chemical structure | Maximum absorbing wavelength (nm) in ethyl cellosolve acetate |
| --- | --- | --- |
| 5 | (structure with NC, =CH-, C₂H₄CN, N, n-C₅H₁₁, OSi(CH₃)₃, NH, phenyl groups) | 424 |
| 6 | (structure with NC, C₂H₅OOC, =CH-, N(C₂H₅)₂, OCOCH₃) | 423 |
| 7 | (structure with NC, =CH-, N(C₂H₄OH)₂, NHC=O, OH, phenyl) | 415 |
| 8 | (structure with NC, NC, =CH-, N(C₂H₅), (CH₂)₆, N(C₂H₅), CH=, CN, CN, OCOCH₃, OCOCH₃) | 433 |
| 9 | (structure with NC, NC, =CH-, N(CH₃), (CH₂)₃, N(CH₃), CH=, CN, CN, OCOCH₃, OCOCH₃) | 435 |
| 10 | (structure with NC, NC, =CH-, N(C₂H₅), (CH₂)₆, N(C₂H₅), CH=, CN, CN, OH, OH) | 419 |
| 11 | (structure with NC, NC, =CH-, N(CH₃), (CH₂)₃, N(CH₃), CH=, CN, CN, OH, OH) | 420 |
| 12 | (structure with NC, NC, =CH-, morpholino-N, OH) | 430 |

EXAMPLES 13 AND 14 AND COMPARATIVE EXAMPLES 1 AND 2

Photoresist compositions were prepared by adding each dye compound shown in Table 2 to a positive photoresist PF-6200 (manufactured by Sumitomo Chemical Company, Limited; a solid content of 31.0% by weight), which comprises a novolak resin (Mw=12,000) prepared mainly from m-cresol and at least one compound having o-quinone diazide groups. The amount of each dye compound added was 0.68% by weight based on the solid amount in the positive photoresist.

Each of the photoresist compositions was coated on a 4 inch square silicon wafer with an aluminum film on its surface by means of a spinner so as to form a resist film of 1.80 μm in thickness. Subsequently, the silicon wafer was baked for 1 minute on a hot plate kept at 100° C., and exposed to light through a test reticule while varying the exposure value stepwise by means of a reduced projection exposing apparatus (Nicon NSR-1505G). Thereafter, the silicon wafer was developed by a static paddle method for 60 seconds at 23° C. in a developing solution SOPD (manufactured by Sumitomo Chemical Company, Limited) by means of an automatic developing machine. The results are summarized in Table 2.

In Comparative Examples 1 and 2, dyes disclosed in Japanese Patent Kokai Publication Nos. 93445/1986 and 37562/1976 were used, respectively.

TABLE 2

| Example No. | Chemical structure | Relative sensitivity | Absorbance ratio |
|---|---|---|---|
| Example 13 | NC\C=CH—◯—N($C_2H_5$)$_2$ / OCOCH$_3$ / NC | 0.5–0.6 | 1.0 |
| Example 14 | NC\C=CH—◯—N($C_2H_5$)$_2$ / OH / NC | 0.5–0.6 | 0.76 |
| Comparative Example 1 | NC\C=CH—◯—N($C_2H_5$)$_2$ / NC | 1.0 | 0.95 |
| Comparative Example 2 | ◯—N=N—◯—N(CH$_3$)$_2$ | 1.9 | 0.75 |

As understood from the results in Table 2, patterns with high sensitivity were formed in Examples of the present invention.

The pattern could be resolved sharply even when the line width was 0.8 μm. No notching caused with the reflected light on the side surfaces of patterns was found. The above results indicate that the photoresist compositions of the present invention impart excellent antihalation effect.

The same compositions were coated on a glass wafer in the same procedures as in case of the aluminum wafer described above.

The glass wafer was prebaked for 30 minutes in a convection oven kept at 120° C., and the absorbance ratio at 436 nm was measured with an UV-visible spectrum meter (comparison with that before prebaking). The effect of decomposition of the sensitizer was neglected. The results showed that the absorbance ratio was about one (1), which indicates that the photoresist compositions of the present invention are excellent in antisublimation.

A silicon wafer was exposed in the same way as above and after-baked for 30 minutes in a convection oven kept at 90° C. After 4 days storage at room temperature, the silicon wafer was developed.

Inspection on deposits remained between patterns revealed that no precipitation was found.

After 6 months storage at 23° C., no light absorber precipitated in the resist composition.

On the contrary, the photoresist compositions of Comparative Examples had insufficient sensitivity and antisublimation.

EXAMPLE 15

A pattern was formed on an aluminum wafer by the same procedures as in Examples 13–14 except that the compound of the formula:

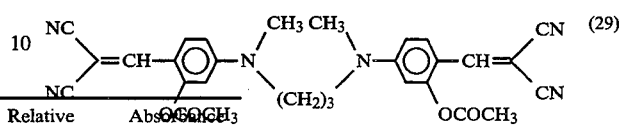

was used in place of the compounds shown in Table 2. The pattern with high sensitivity was formed.

The pattern could be resolved sharply and no notching caused with the reflected light on the side surface of the patterns was found.

The photoresist composition in this Example is also excellent in antisublimation. Inspection on deposits remained between the patterns revealed that no precipitation was found.

Reference Example 1

(synthesis of the light absorber)

A mixture of 16.5 g (0.1 mol) of (N-ethyl-N-hydroxyethyl)aniline, 0.5 ml of pyridine and 12.3 g of acetic anhydride was stirred for 20 hours at 40°–50° C.

After cooling the mixture down to 20°–23° C., 5 ml of methanol was added to the mixture and then stirred for 1 hour. The resulting mixture was extracted three times with 500 ml of water and 200 ml of ethyl acetate.

Thereafter, the upper layer was filtered, and the filtrate was concentrated to obtain 20.7 g of (N-ethyl-N-acetoxyethyl)aniline.

20.7 Grams of (N-ethyl-N-acetoxyethyl)aniline thus obtained was dissolved in 25 ml of DMF (dimethylformamide). 13.5 Milliliters of phosphorus oxychloride were dropwise added over 12 minutes at about 40° C. while stirring. The mixture was stirred for 6 hours at 60°

C. and thereafter allowed to cool down to 30° C. Then the solution was poured into 100 ml of ethanol.

Then 30 ml of a 25% aqueous ammonia solution and 6.6 g of malonic nitrile were added, and the condensation reaction was carried out for 5 hours at 70° C. while refluxing.

After cooling down to 10°-20° C., the resulting precipitate was filtered off.

The filtrate contained about 50% of a compound of the formula.

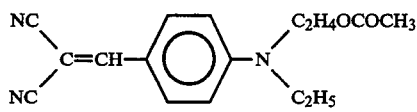

The filtrate was added to 40 ml of ethanol and the resulting mixture was heated at 75° C. while stirring. Then 15 ml of 37% hydrochloric acid was poured. The mixture was then reacted for 30 minutes under reflux conditions.

Thereafter the solution was allowed to cool down to about 60° C., and then poured in iced water to precipitate crystal.

The resulting crystal was filtered, washed with water and dried to obtain 19.2 g of 4-(N-ethyl-N-hydroxyethyl)amino-$\beta,\beta$-diciano styrene of the formula:

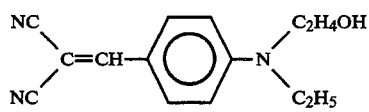

Reference Example 2

About 17.5 g of 4-(N-hexyl-N-hydroxyhexyl)amino-$\beta,\beta$-dicianostyrene of the formula:

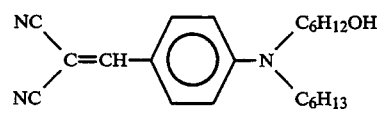

was obtained by the same procedures as in Reference Example 1 except that an amino compound of the formula:

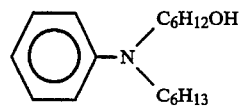

which had been obtained by the reaction of 0.1 mol of a compound of the formula:

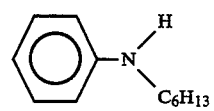

with $Cl(CH_2)_6OH$, was used in place of 16.5 g of (N-ethyl-N-hydroxy ethyl)aniline.

EXAMPLES 16 to 18

Into PF-6200 (which was used in Examples 13–14 and Comparative Examples 1–2), each of the compounds shown in Table 3 was added to prepare photoresist compositions.

The amount of the compound was 0.68% by weight based on the solid amount in PF-6200.

Each of the photoresist compositions was coated on a 4 inch silicon wafer with an aluminum film on its surface by means of a spinner so as to form a resist film of 1.80 μm in thickness.

The coated silicon wafer was baked for 1 minute on a hot plate kept at 100° C., and exposed and developed in the same procedures as in Examples 13 and 14. The results are shown in Table 3.

TABLE 3

| No. | Chemical structure | Relative sensitivity | Absorbance ratio |
| --- | --- | --- | --- |
| Example 16 | NC\C=CH—⟨○⟩—N(C₂H₄OH)(C₂H₅) | 0.6 | 0.97 |
| Example 17 | NC\C=CH—⟨○⟩—N(C₂H₄OH)(C₂H₄CN) | 0.6 | 0.98 |
| Example 18 | NC\C=CH—⟨○⟩(CH₃)—N(C₂H₄OH)(C₂H₅) | 0.6 | 1.0 |
| Comparative Example 1 | NC\C=CH—⟨○⟩—N(C₂H₅)₂ | 1.0 | 0.95 |

TABLE 3-continued

| No. | Chemical structure | Relative sensitivity | Absorbance ratio |
|---|---|---|---|
| Comparative Example 2 | 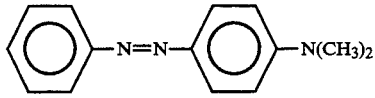 | 1.9 | 0.75 |

As understood from the results in Table 3, patterns with high sensitivity were formed in Examples of the present invention.

The pattern could be resolved sharply even when the line width was 0.8 μm. No notching caused with the reflected light on the side surfaces of patterns was found. The above results indicate that the photoresist compositions of the present invention impart excellent antihalation effect.

The same compositions were coated on a glass wafer in the same procedures as in case of the aluminum wafer described above.

The glass wafer was prebaked for 30 minutes in a convection oven kept at 120° C., and the absorbance ratio at 436 nm was measured with an UV-visible spectrum meter (comparison with that before prebaking). The effect of decomposition of the sensitizer was neglected. The results showed that the absorbance ratio was about one (1), which indicates that the photoresist compositions of the present invention are excellent in antisublimation.

A silicon wafer was exposed in the same way as above and after-baked for 30 minutes in a convection oven kept at 90° C. After 4 days storage at room temperature, the silicon wafer was developed.

Inspection on deposits remained between patterns revealed that no precipitation was found.

After 6 months storage at 23° C., no light absorber precipitated in the resist composition.

On the contrary, the photoresist compositions of Comparative Examples had insufficient sensitivity and antisublimation.

EXAMPLE 19 AND COMPARATIVE EXAMPLE 3

In these Examples, used was a meta-cresol novolak resin characterized in that the area ratio in the gel permeation chromatographic pattern (GPC pattern) was as follows:

A range wherein the molecular weight is larger than 150 and less than 500 (not including a phenol and the unreacted monomer) was 18.2%, a range wherein the molecular weight is more than 500 and less than 5,000 was 20.8% and a range wherein the molecular weight exceeds 5,000 is 61.0%.

In the same way as described in European Patent Publication No. 271199, 17 parts (by weight) of the novolak resin, 5.25 parts of a condensation product of naphthoquinone-(1,2)-diazide-(2)-5-sulfonic acid chloride with 2,3,4-trihydroxybenzophenone and 0.15 parts of each compound shown in Table 4 were dissolved in 49.25 parts of ethyl cellosolve acetate.

The mixture was filtrated through a 0.2 μm filter to obtain a photoresist composition.

On a silicon wafer on which aluminum had been deposited in a thickness of 1 μm, the photoresist composition was coated by means of a spin coater. Then the coated silicon wafer was baked for 1 minute on a hot plate kept at 100° C. The photoresist film thickness after bake was 1.28 μm.

Thereafter, patterns were formed in the same way as in Example 16. These results are summarized in Table 4.

TABLE 4

| No. | Chemical structure | Relative sensitivity |
|---|---|---|
| Example 19 | 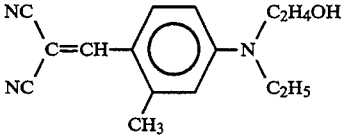 | 0.6 |
| Comparative Example 3 | 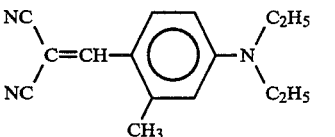 | 1.0 |

As understood from the results in Table 4, the photoresist composition of Example 19 of the present invention imparted high sensitivity, and the formed patterns could be resolved sharply even when the line width was 0.7 μm.

No notching due to reflected light on the side surfaces of the patterns or no distortion of the patterns could be found, and excellent antihalation effect was achieved.

In addition, excellent antisublimation was also achieved and no deposit of the light absorber could be found.

EXAMPLES 20 to 23

Patterns were formed on an aluminum wafer by the same procedures as in Example 19 except that each compound in Table 5 was used.

TABLE 5

| No. | Chemical structure |
|---|---|
| Example 20 | 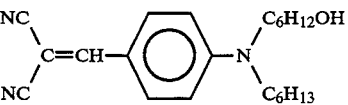 |
| Example 21 | 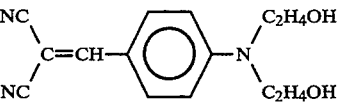 |
| Example 22 | 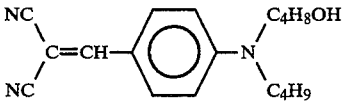 |

TABLE 5-continued

| No. | Chemical structure |
|---|---|
| Example 23 | 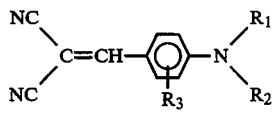 |

In each Example, the relative sensitivity is as high as 0.5 to 0.7, and the formed patterns could be resolved sharply even when the line width was 0.7 μm. No notching due to the light reflection on the side surfaces of the patterns was found. The antisublimation was good and no precipitation of the light absorber was found.

What is claimed is:

1. A photoresist composition which comprises a sensitizing compound, a resin and, as a light absorber, styryl compound of the general formula (I) or (II):

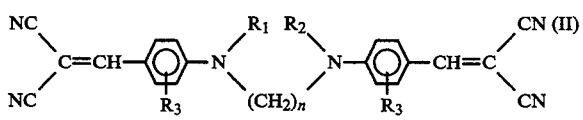

wherein $R_1$ and $R_2$ are the same or different and are a hydrogen atom; a $C_1$-$C_{10}$ alkyl group; a $C_1$-$C_{10}$ alkyl group substituted with —OH, —CN, —COOH, —SO$_3$H, —NHSO$_3$H, —Cl, —Br, —F, —I or —COOR$_{14}$ in which R$_{14}$ is a lower alkyl group; a $C_2$-$C_{10}$ alkenyl group; a $C_2$-$C_{10}$ alkenyl group substituted with —OH, —CN, —COOH, —SO$_3$H, —NHSO$_3$H, —Cl, —Br, —F, —I or —COOR$_{14}$ in which R$_{14}$ is a lower alkyl group; or

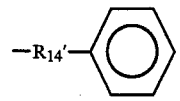

in which $R_{14}'$ is a lower alkylene group;
$R_3$ is —OCOR$_5$ or —OSi(R$_5$)$_3$ in which R$_5$ is a lower alkyl group; and n is a number of 2 to 15.

2. A composition of claim 1 comprising a compound of the formula

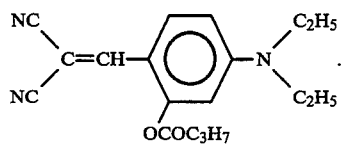

3. A composition of claim 1 comprising a compound of the formula

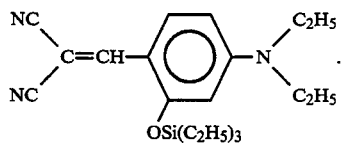

4. A composition of claim 1 comprising a compound of the formula

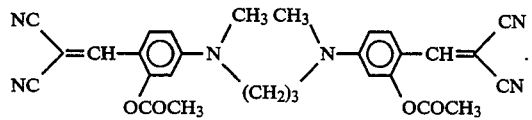

5. A composition of claim 1 comprising a compound of the formula

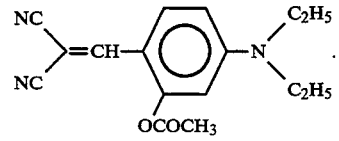

* * * * *